United States Patent
Perot et al.

(10) Patent No.: US 11,376,358 B2
(45) Date of Patent: Jul. 5, 2022

(54) PACKAGING FOR A PREFILLED DRUG DELIVERY DEVICE

(71) Applicant: Becton Dickinson France, Le Pont de Claix (FR)

(72) Inventors: Frédéric Perot, Saint Paul de Varces (FR); Julien Gagliano, Grenoble (FR); Marie-Liesse Le Corfec, Lyons (FR); Hervé Monchoix, Montbonnot Saint-Martin (FR)

(73) Assignee: Becton Dickinson France, Le Pont de Claix (FR)

( * ) Notice: Subject to any disclaimer, the term of this patent is extended or adjusted under 35 U.S.C. 154(b) by 181 days.

(21) Appl. No.: 16/967,585

(22) PCT Filed: Feb. 5, 2019

(86) PCT No.: PCT/EP2019/052753
§ 371 (c)(1),
(2) Date: Aug. 5, 2020

(87) PCT Pub. No.: WO2019/154796
PCT Pub. Date: Aug. 15, 2019

(65) Prior Publication Data
US 2021/0236713 A1 Aug. 5, 2021

(30) Foreign Application Priority Data

Feb. 7, 2018 (EP) ..................................... 18305128

(51) Int. Cl.
*A61M 5/00* (2006.01)
*A61M 5/32* (2006.01)

(52) U.S. Cl.
CPC .......... *A61M 5/002* (2013.01); *A61M 5/3204* (2013.01); *A61M 5/3205* (2013.01); *A61M 2209/06* (2013.01)

(58) Field of Classification Search
CPC .. A61M 5/002; A61M 5/3204; A61M 5/3205; A61M 2209/06
USPC .................................................. 206/363, 364
See application file for complete search history.

(56) References Cited

U.S. PATENT DOCUMENTS

| | | |
|---|---|---|
| 5,137,516 A | 8/1992 | Rand et al. |
| 2011/0272310 A1* | 11/2011 | Tennican .............. A61M 5/002 604/82 |
| 2012/0001750 A1* | 1/2012 | Monroe ................ A61M 5/002 340/539.11 |
| 2014/0224688 A1 | 8/2014 | Slemmen et al. |
| 2014/0251847 A1 | 9/2014 | Jeter et al. |
| 2017/0088333 A1* | 3/2017 | Devouassoux .... A61K 31/5415 |

* cited by examiner

*Primary Examiner* — Jacob K Ackun
(74) *Attorney, Agent, or Firm* — The Webb Law Firm (57) ABSTRACT

A packaging for storing a drug delivery device comprising a container provided at its distal end with a distal tip bearing a needle, the needle being covered by a shield, the packaging comprising: a support comprising: a first holding element configured for receiving at least part of the shield before use, a second holding element configured for receiving a distal part of the needle after use, and an envelope for receiving the drug delivery device, the envelope being closed by the support.

17 Claims, 7 Drawing Sheets

PACKAGING FOR A PREFILLED DRUG DELIVERY DEVICE

CROSS-REFERENCE TO RELATED APPLICATIONS

This application is the United States national phase of International Application No. PCT/EP2019/052753 filed Feb. 5, 2019, and claims priority to European Patent Application No. 18305128.3 filed Feb. 7, 2018, the disclosures of which are hereby incorporated by reference in their entirety.

BACKGROUND OF THE INVENTION

The present invention relates to a packaging for storing and transporting a drug delivery device, in particular a prefilled drug delivery device.

In the present application, the distal end of a piece or a device is understood to be the end furthest from the hand of the user and the proximal end is understood to be the end closest to the hand of the user. Likewise, in the present application, "distal direction" is understood to be the direction of injection, and "proximal direction" is understood to be the direction opposite the direction of injection.

A drug delivery device such as, for example, a syringe, must be handled with care before and after use due to the presence of a needle. To preserve sterility of the drug contained into the syringe and tightness of the syringe, but also to minimize the risk of accidental needle-stick injury, syringes are typically supplied with a needle shield that covers the sharpened tip of the needle. The needle shield is removed prior to use to expose the sharpened tip of the needle and perform the injection.

After use, the user must be able to discard the drug delivery device without having to take the risk to be injured by the used needle. Procedures in the medical field require that the user recovers the needle by a protection device before throwing away the used drug delivery device into an appropriate container.

Some illnesses, such as multiple sclerosis or arthritis, necessitate that a drug be injected into a patient regularly, such as every day or every week. The drug is available under the form of prefilled drug delivery devices, such as prefilled syringes. Usually, the patient is trained to self-injection and is capable to proceed to the injection of the drug by himself.

Anyway, when the patient needs to travel for a significant time period, he needs to bring the drug with him, for example under the form of a prefilled syringe. Prefilled syringes are items that need to be transported cautiously. Moreover, once used, the needle of the syringe should be protected to avoid accidental needle sticks. In addition, used prefilled syringes with needles must be discarded in specific containers intended for receiving sharp items such as needles, as well as potential contaminated medical devices.

There is therefore a need for a packaging allowing safe storage and transportation of a prefilled drug delivery device or syringe, before and after use.

BRIEF SUMMARY OF THE INVENTION

The present invention relates to a packaging for storing at least one drug delivery device comprising a container provided at its distal end with a distal tip covered by a shield in a before-use storage configuration of the drug delivery device, said shield being intended to be removed from said distal tip at time of use and a distal end of said distal tip being intended to bear a needle during use of the drug delivery device, the packaging comprising:

a support comprising at least:

one first holding means or first holding element configured for receiving at least part of said shield in the before-use storage configuration of said drug delivery device, one second holding means or second holding element configured for receiving at least a distal part of said needle when said needle is born by said distal tip in an after-use storage configuration of said drug delivery device, and an envelope configured to enclose said drug delivery device, when said shield is received in said first holding means or first holding element in the before-use storage configuration of the drug delivery device and when said distal part of said needle is received in said second holding means or second holding means in the after-use storage configuration of said drug delivery device, said envelope being configured to be closed by said support.

The packaging of the invention is particularly intended to be used for storing a prefilled drug delivery device. For example, the envelope is configured to enclose the prefilled drug delivery device before use of said drug delivery device, when the shield is received within the first holding means or first holding element, and to enclose the drug delivery device after use, when at least a distal part of the needle is received within said second holding means or second holding element.

The packaging of the invention allows storing, transporting, using and discarding a prefilled drug delivery device safely. In particular, thanks to the packaging of the invention, the drug delivery device is located at a specific location of the packaging before use and at a further specific location of the packaging after use and it may be transported safely before and after use before being discarded in an appropriate container.

In embodiments, the packaging of the invention may allow storing more than one prefilled drug delivery device. For example, the support may comprise more than one first holding means or first holding element and/or more than one second holding means or second holding element, thereby allowing storing a plurality of prefilled drug delivery devices before and after use.

In embodiments, said second holding means or second holding element are configured for further receiving at least a distal part of said distal tip. For example, the second holding means or second holding element are configured for receiving the whole needle and a distal part of the distal tip, when the drug delivery device is in the after-use storage configuration.

In the present document, by the expression "the needle is born by the distal tip" is meant that the needle may be born either directly by the distal tip of the drug delivery device, in which case the needle is usually a staked or an overmoulded needle, or via a needle hub mounted onto the distal tip of the drug delivery device, in which case the distal tip as such is free of any needle.

When the needle is born directly by said distal tip in the before-use storage configuration of said drug delivery device, the shield is preferably configured for covering said needle. For example, the shield may be made of a rigid material. The shield allows therefore protecting the needle and its distal end so that accidental needle stick injuries may be avoided. Suitable rigid materials for forming such rigid needle shields may be selected from polyethylene, polypropylene, polycarbonate and/or combinations thereof. The shield may further comprise a part made of a soft material such as rubber, elastomeric polymer and/or combinations thereof.

Alternatively, when the distal tip is free of any needle in the before-use storage configuration of said drug delivery device, the shield may then be made of a material selected from rubber, elastomeric polymers and/or combinations thereof. The packaging may therefore further comprise a needle hub bearing a needle, said needle hub being configured for being mounted onto a distal end of said distal tip once the shield has been removed from said distal tip.

In embodiments, the first holding means or first holding element and the second holding means or second holding element are fixed to said support, for example in a permanent way. This allows the drug delivery device to be safely positioned before and after use.

Alternatively or in combination, the support may have the shape of a rigid shell, for example having a bottom wall.

The support of the packaging of the invention may be used for removing the shield from the drug delivery device bearing the needle before use. Indeed, prefilled drug delivery devices may be used on a regular basis by patients suffering for example from arthritis. Due to arthritis, patients' fingers hurt and are no more capable of completing precise and effort demanding gestures. These patients regularly experiment difficulties in removing the shield protecting the distal tip of the drug delivery device, as it requires to firmly handle relatively small items using both hands, like the shield on one hand, and the container of the drug delivery device on the other hand. Thanks to the packaging of the invention, the patients may use the whole support in lieu and place of the shield during the operation of removing the shield from the drug delivery device. This removal step is therefore facilitated for them.

In embodiments, the first holding means or first holding element comprise a first cavity configured to receive at least part of said shield and first gripping means or a first gripping element configured to retain said shield fixed to said cavity. The first gripping means or first gripping element may be further configured to retain said shield within said cavity in a permanent way. The patient is therefore ensured that the shield will remain into the support when he removes the drug delivery device from the shield before use.

For example, a proximal end of said shield being attached onto said distal tip, said first gripping means or first gripping element comprise flexible legs capable of being snap-fitted onto said proximal end of said shield. Alternatively or in combination, said first gripping means or first gripping element may hold the shield onto a distal end of said shield.

In embodiments, the second holding means or second gripping element comprise a second cavity configured to receive at least a distal part of said needle. Advantageously, the second cavity is configured to further receive at least a distal part of said distal tip. The second holding means or second holding element may comprise second gripping means or a second gripping element configured to retain said distal part of said distal tip within said second cavity. The needle and the distal part of the distal tip are therefore safely positioned after use, the needle being contained within said second cavity. The user and any other person who could come into contact with the device are therefore protected from accidental needle-stick injuries that could occur with the used needle.

In embodiments, the second gripping means or second gripping element comprise flexible tongs retaining said distal part of said distal tip by friction-fit engagement.

Alternatively or in combination, the second cavity may comprise an inner plug configured for embedding a distal part of the needle. By inserting the needle within the plug, the plug may also help, in addition to the gripping means or gripping element, in securing the used drug delivery device in a stable position into the packaging after use.

In embodiments, the support and the envelope form a rigid case.

The support may comprise a distal transversal wall forming a bottom of the rigid shell and may be easily positioned on a table so that the user may hold the shell with one hand and, with the other hand:

either remove the drug delivery device from the first holding means or first holding element of the support, optionally mount a needle hub bearing a needle onto the distal tip of the drug delivery device if the distal tip is free of any needle, in order to proceed to the injection, and/or insert the drug delivery device bearing the needle inside the second holding means or second holding element of the support after use in order to protect the used needle.

In embodiments, said first cavity has an elongated shape extending proximally from the support along a first longitudinal axis C and said second cavity has an elongated shape extending proximally from the support along a second longitudinal axis D. For example, said first cavity and said second cavity may have a cylindrical shape, such as a sleeve. The first cavity may have a length longer than that of the second cavity, so that for example a proximal end of the first cavity extends beyond a proximal end of the second cavity in the proximal direction. The proximal end of the first cavity may in addition extend beyond a proximal end of the support in the proximal direction. The risk that the drug delivery device touch the support and/or the second holding means, such as the second cavity, when the drug delivery device is removed from the first holding means, such as the first cavity, is therefore reduced. The risk that the drug delivery device be contaminated before injection through contact with the support and/or the second holding means is therefore decreased.

In embodiments, said first longitudinal axis C and second longitudinal axis D are parallel to each other. The first cavity and the second cavity may for example extend parallel to each other from a common wall of the support.

In embodiments, wherein said envelope extends proximally from said support along a central longitudinal axis B, said first and second cavities are located on either side of a plane including said central longitudinal axis B, said first and second longitudinal axes C and D being inclined towards said central longitudinal axis B, so that a proximal end of the container of said drug delivery device is substantially located on the central longitudinal axis B when said shield is received in said first holding means or first holding element in the before-use storage configuration of the drug delivery device or when said distal part of said needle is received in said second holding means or second holding element in the after-use storage configuration of said drug delivery device. In such embodiments, in particular, when the support and the envelope form together a rigid case, such an arrangement of the first and second cavities allow the drug delivery device to be held sufficiently away from a wall of the envelope when said drug delivery device is stored within the packaging, while providing a compact packaging easy to transport. The inclination of the first cavity and/or of the second cavity allows obtaining a compact radial design for the packaging, even if the drug delivery device stored therein comprises an extended flange.

In embodiments, the packaging further comprises a tactile and/or visual indicator configured to inform a user that the distal part of said needle is received in said second holding means or second holding element in the after-use storage configuration of said drug delivery device.

For example, said indicator comprises a peg capable of circulating in an open channel provided in a wall of the support and communicating with said second cavity, said peg being capable of moving from a retracted position, in which said peg is neither visible nor feelable by a user to an exposed position in which said peg may be seen and/or felt by the user, said peg being caused to move from said retracted position to said exposed position upon insertion of the distal part of said needle into said second cavity.

In alternative embodiments, the envelope comprises a film having a resealable opening. The packaging may therefore be opened through said opening in order to remove the drug delivery device from the packaging and therefore proceed to the injection. After injection, once the used needle has been inserted into the second holding means or second holding element, the user may reseal the opening in the film, and thereby close the packaging. He may then safely carry the packaging holding the drug delivery device with the used needle until he discards the whole packaging into an appropriate container.

In embodiments, the packaging may further comprise medical items selected from anesthetic pads, alcohol swabs, sticky plasters and combinations thereof, for example located within the envelope. The packaging may further comprise instructions for use, for example printed onto the film forming the envelope, or printed onto a folded sheet inserted into the envelope.

In embodiments, the packaging may further comprise a sheet bearing instructions for use, said sheet being folded on itself and positioned between the drug delivery device stored in said packaging in its before-use storage configuration and an inner wall of the envelope, so that said sheet pops up from the packaging when a user removes the envelope from the support. In embodiments, said sheet may be folded on itself and over a piston rod of the drug delivery device. In other embodiments, the sheet may be folded on itself in a concertinaed way and sandwiched between a proximal end of the plunger rod and an inner surface of a proximal wall of the envelope. A proximal end of the sheet may be removably attached to said inner surface of a proximal wall of the envelope and a distal end of the sheet may be removably attached to the proximal end of the plunger rod. The sheet may therefore be unfolded and further detached by the user as he removes the envelope from the support. The use of the packaging is therefore facilitated for the user as he needs not looking for the instructions for use, such instructions for use being made readily available for him.

The invention also relates to packaging for storing at least one drug delivery device including a container provided at its distal end with a distal tip covered by a shield in a before-use storage configuration of the drug delivery device, said shield configured to be removed from said distal tip at time of use and a distal end of said distal tip configured to bear a needle during use of the drug delivery device. The packaging includes a support including at least one first holding element configured for receiving at least part of said shield in the before-use storage configuration of said drug delivery device, one second holding element configured for receiving at least a distal part of said needle when said needle is born by said distal tip in an after-use storage configuration of said drug delivery device, and an envelope configured to enclose said drug delivery device, when said shield is received in said first holding element in the before-use storage configuration of the drug delivery device and when said distal part of said needle is received in said second holding element in the after-use storage configuration of said drug delivery device, said envelope configured to be closed by said support.

BRIEF DESCRIPTION OF DRAWINGS

The invention will now be described in details, with reference to the enclosed drawings in which.

DETAILED DESCRIPTION OF THE INVENTION

Figure 1:
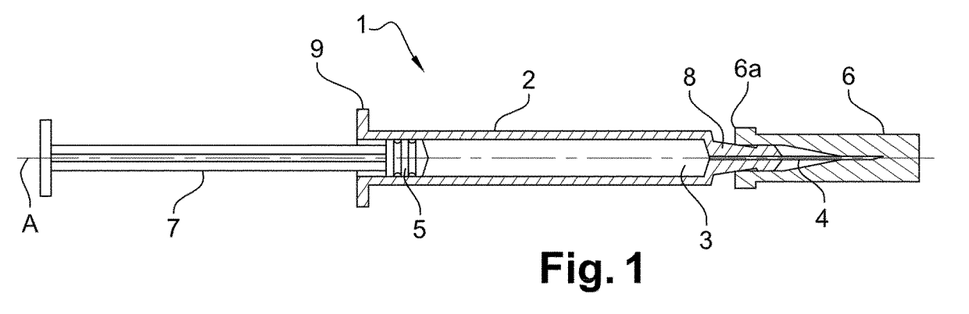
FIG. 1 is a cross section view of a prefilled drug delivery device comprising a distal tip bearing a needle and a shield protecting the needle.

With reference to FIG. 1 is shown a prefilled drug delivery device 1 having a longitudinal axis A. The prefilled drug delivery device 1 comprises a container 2 for receiving the drug 3 to be injected. In the example shown in FIG. 1, the container 2 comprises at its distal end a distal tip 8 bearing a needle 4. In the example shown, the needle 4 is directly born by the distal tip 8. The container 2 is closed at its proximal end by a stopper 5. In the before-use storage configuration of the drug delivery device 1, as shown in FIG. 1, the needle 4 is covered by a shield 6 so as to protect it from outside contamination and so as to ensure tightness with the drug 3 contained into the container 2. The shield 6 further protects the user from accidental needle-stick injuries. The shield 6 is preferably made from a rigid material. Suitable materials for forming the shield 6 may be selected from polyethylene, polypropylene, polycarbonate and/or combinations thereof. The shield 6 may further comprise a part made of a soft material such as rubber, elastomeric polymer and/or combinations thereof.

In the example shown, a piston rod 7 is attached to the stopper 5. In embodiments not shown, the piston rod could be separate from the stopper 5.

In the example shown in FIG. 1, the proximal end 6a of the shield 6 is attached to the distal tip 8 of the drug delivery device 1. Moreover, the container 2 is provided at its proximal end with a flange 9. The flange 9 may help the user hold the drug delivery device 1 with the index and middle fingers while his thumb is pushing on the piston rod 7.

Figure 2:
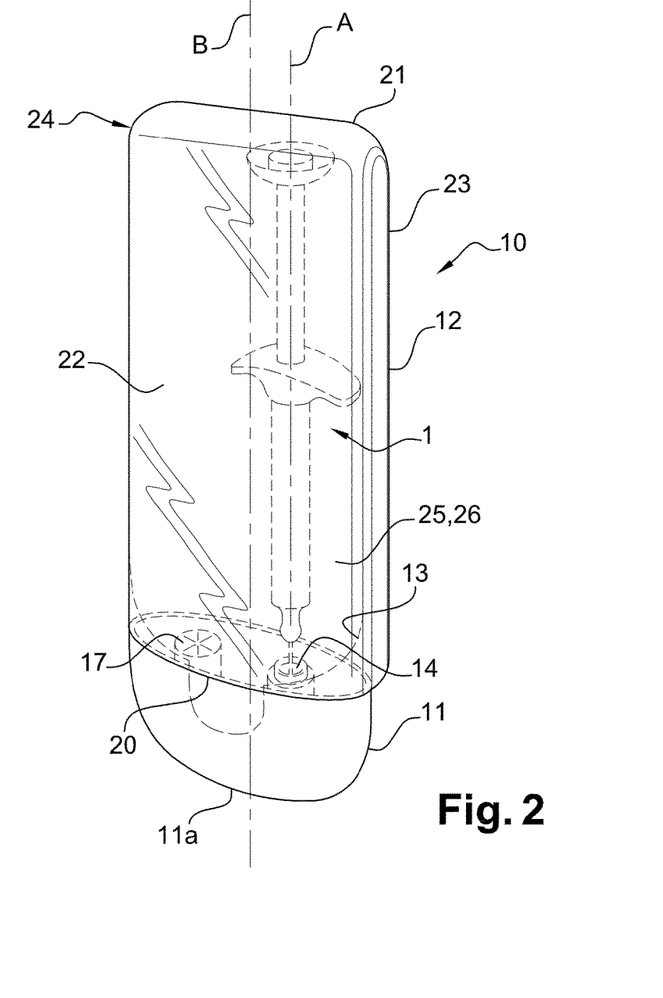
FIG. 2 is a perspective view of a first embodiment of a packaging of the invention with a prefilled drug delivery device contained therein.

With reference to FIG. 2, is shown a first embodiment of a packaging 10 of the invention. The packaging 10 comprises a support 11 and an envelope 12. The envelope 12 is shaped and dimensioned so as to enclose the prefilled drug delivery device 1 before use, when the shield 6 is received within first holding means or a first holding element described below, as well as to enclose the drug delivery device 1 after use, when at least a distal part of the needle is received within second holding means or a second holding element further described below.

The envelope 12 preferably extends proximally from the support 11 along a longitudinal axis B.

The envelope 12 preferably comprises:
An open distal end 20 closed by the support 11,
A proximal end 21 which is closed,
A front side 22, and
A back side 23.

In embodiments, instructions for use may be printed on the front side 22 of the envelope 12 or on a label attached to the front side of the envelope 12. Alternatively, instructions for use may be folded and inserted into the packaging such as shown on FIG. 14. Although not shown, the packaging 10 may further include medical items such as for example anesthetic pads, alcohol swabs or sticky plasters, that may be located within the envelope.

The packaging 10 is preferably configured to be:
open so a user may have access to the drug delivery device located within the packaging, and/or
closed to prevent access to a drug delivery device located within the packaging.

To that purpose, according to one embodiment, the envelope may be removably attached to the support. According to this embodiment, the envelope forms a removable closure from the support, the envelope being configured to be:
either attached to the support in order to form with the support a pouch enclosing the drug delivery device when it is at least partially inserted into one of the first or second holding means, or one of the first or second holding elements, of the support; or
removed from the support.

According to an embodiment, the envelope may be permanently fixed to the support. In such an embodiment, the envelope comprises an opening 13 allowing access to the drug delivery device enclosed into the envelope. In embodiments, the opening 13 is a resealable opening.

According to the embodiment of FIGS. 2-6, the envelope 12 may comprise a rigid part and a flexible part. For example, as represented on FIG. 2, the envelope 12 may comprise a rigid frame 24 supporting a flexible film 25. For example, the rigid frame 24 may present a U-shaped body supporting a front part 26 of the flexible film 25 closing the front side 22 of the envelope 12 and a back part 27 (see FIGS. 5 and 6) of the flexible film 25 closing the back side 23 of the envelope 12. Alternatively, in embodiments not shown, the envelope may comprise a rigid shell and an opening lid attached to the rigid shell via a hinge. Alternatively, the envelope may comprise a back rigid shell and a front flexible film. The flexible film may be for example a plastic film, such as a polypropylene film or a polyethylene film.

With reference to FIGS. 2-6, the support 11 has the shape of a rigid shell. The rigid shell has a bottom wall 11a. Suitable materials for forming the rigid shell may be selected from polypropylene, polyoxymethylene, polycarbonate, acrylonitrile butadiene styrene and/or combinations thereof.

With reference to FIGS. 2-6, the support 11 is configured so as to be able to stand in a substantially stable position when positioned on a horizontal surface, so that the drug delivery device 1 extends substantially vertically when it is at least partially inserted into one of the first or second holding means, or one of the first or second holding elements, of the support, as will appear from the description below.

The support 11 comprises first holding means or first holding element configured for receiving at least part of the shield 6 of a prefilled drug delivery device 1, such as the one shown in FIG. 1. The first holding means or first holding element may be configured to retain the shield of the drug delivery device when the drug delivery device is pulled out from the support. The first holding means or first holding element are then configured to remove the shield from a drug delivery device. To that purpose, the first holding means or first holding element may comprise a first cavity configured to receive the shield and first gripping means or first gripping element configured to retain the shield within the cavity.

Figure 3:
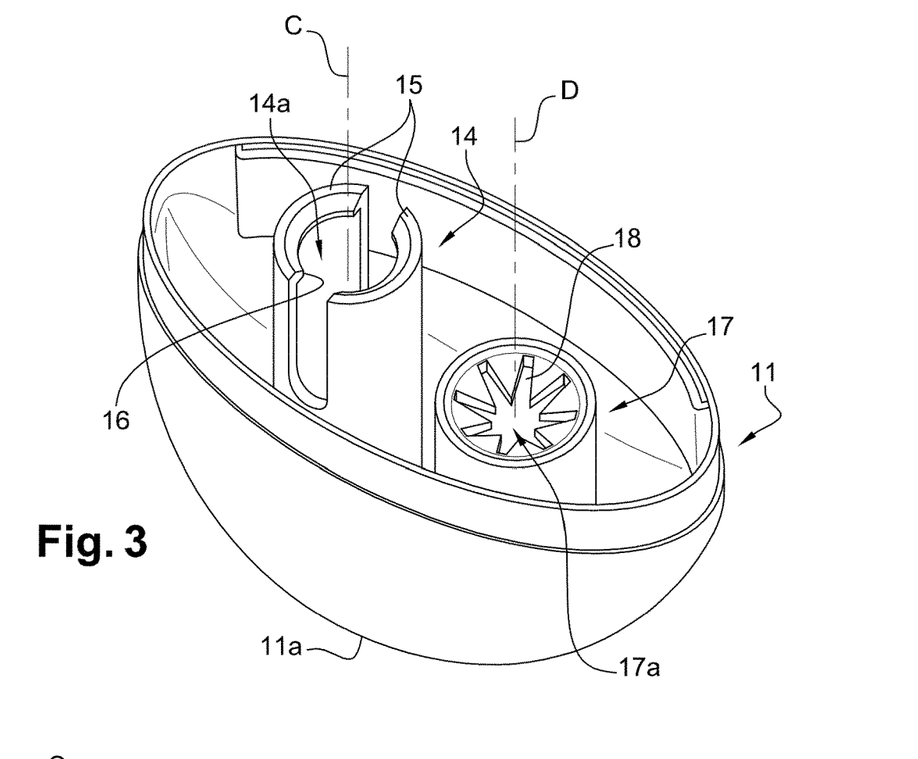
FIG. 3 is a perspective top view of the support of the packaging of FIG. 2.
Figure 4:
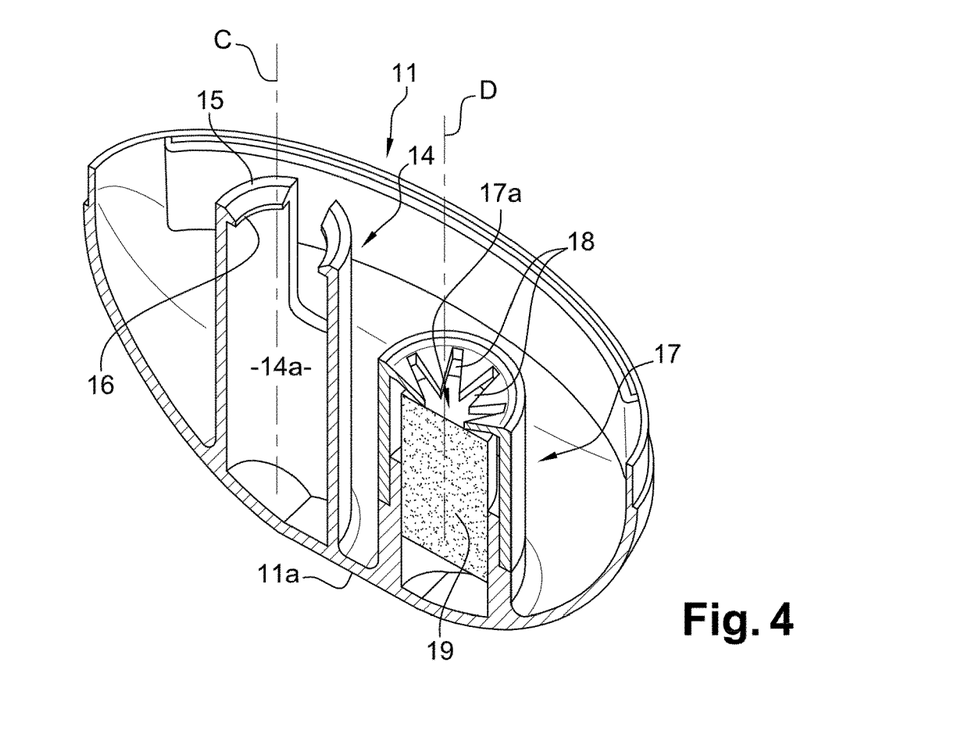
FIG. 4 is a cross section perspective view of the support of FIG. 3.

On the example shown on FIGS. 3 and 4, the first holding means or first holding element comprise a first cavity 14a defined by an elongate casing 14 extending proximally from the support 11 along a first longitudinal axis C, the first cavity 14a being shaped and dimensioned so as to be capable of receiving the shield 6 of the prefilled drug delivery device 1, such as the one shown in FIG. 1, before use.

The distal end of the elongate casing 14 is closed by the bottom wall 11a as shown on FIG. 4. In the example shown, the elongate casing 14 has a cylindrical shape and is fixed to the bottom wall 11a of the rigid shell 11 in a permanent way. The elongate casing 14 is provided at its proximal end with flexible legs 15 provided with an inner rim 16. The shield 6 may therefore be retained within the first cavity 14a thanks to the flexible legs 15 being snap-fitted onto said proximal end of said shield 6.

The support 11 further comprises second holding means or second holding element configured for receiving at least a distal part of the needle and optionally a distal part of the distal tip after use, preferably permanently. To that purpose, the second holding means or second holding element preferably comprise a second cavity configured to receive the needle and a distal part of the distal tip and second gripping means or second gripping element configured to retain the needle and at least a part of the distal tip within the second cavity.

On the example shown on FIGS. 2-6, the second holding means or second holding element comprise a second cavity 17a, defined by an elongated lodging 17 extending proximally from the support 11 along a second longitudinal axis D, the second cavity 17a being shaped and dimensioned so as to be capable of receiving the used needle 4 and a distal part of the distal tip 8 of the drug delivery device 1 after use. On the example shown, the elongated lodging 17 has a cylindrical shape and is provided at its proximal end with radial flexible tongs 18 forming second gripping means or second gripping element for retaining the used needle and the distal tip 8 inside the elongated lodging 17 after use. In particular, the flexible tongs 18 may retain the distal tip 8 inside the elongated lodging 17 by friction-fit engagement or retention teeth engagement.

With reference to FIG. 4, the second cavity 17a comprises an inner plug 19 in which the distal end of the needle 4 may be embedded.

Suitable materials for forming the inner plug 19 may be selected from rubber, elastomeric polymers and/or combinations thereof.

The presence of the inner plug 19 allows maintaining the used drug delivery device 1 in a stable position once repositioned into the packaging 10.

In the example shown in FIGS. 3 and 4, the first cavity 14a and the second cavity 17a are located close to each other and their longitudinal axes are parallel to each other, in the support 11. The packaging 10 is therefore compact. Moreover, as appears from FIGS. 3 and 4, the proximal end of the elongate casing 14 extends beyond the proximal end of the elongated lodging 17 in the proximal direction and further extends beyond the proximal end of the support 11 in the proximal direction.

With reference to FIGS. 2-6, the use of the packaging 10 will now be described.

With reference to FIG. 2, the packaging 10 is shown before use. The shield of the drug delivery device 1 is retained within the first cavity 14a. The envelope 12 encloses the drug delivery device 1 and closes the packaging 10. As appears from this Figure, in the before-use position of this embodiment, the drug delivery device 1 extends substantially parallel to the longitudinal axis B of the packaging 10.

Figure 5:
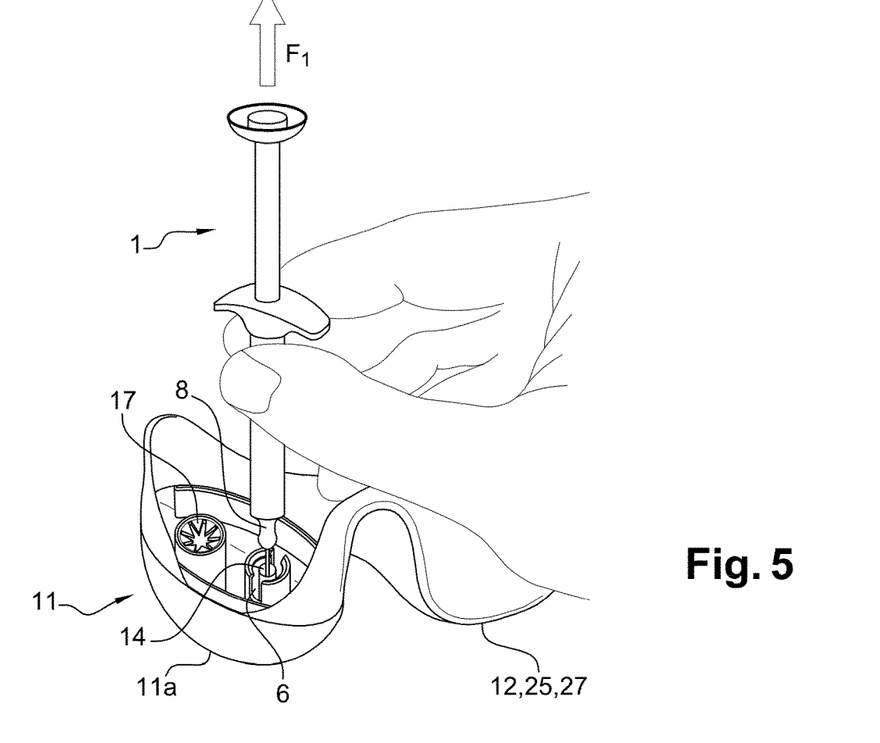
FIG. 5 is a perspective view of the step of removing the drug delivery device from the packaging of FIG. 2.

Once the user wishes to use the drug delivery device 1, he opens the envelope 12 via the opening 13. With reference to FIG. 5, the user then removes the drug delivery device 1 from the elongate casing 14, while the shield 6 remains retained within the first cavity 14a thanks to the flexible legs 15 being snap-fitted onto the proximal end of the shield 6. The user may pull on the drug delivery device 1 in the direction of the arrow F1 of FIG. 5 with one hand, while maintaining the support 11 with the other hand (not shown). The step of removing the shield from the needle is therefore facilitated for people suffering from arthritis for example. The needle is therefore uncovered and the user may use the device in order to proceed to the injection. In addition, since the proximal end of the elongate casing 14 extends beyond the proximal ends of the elongated lodging 17 and of the support 11, the risk that the drug delivery device 1 touch the support 11 and/or the elongated lodging 17 when the drug delivery device 1 is removed from the elongate casing 14 is reduced. The risk that the drug delivery device 1 be contaminated before injection is therefore decreased.

Figure 6:
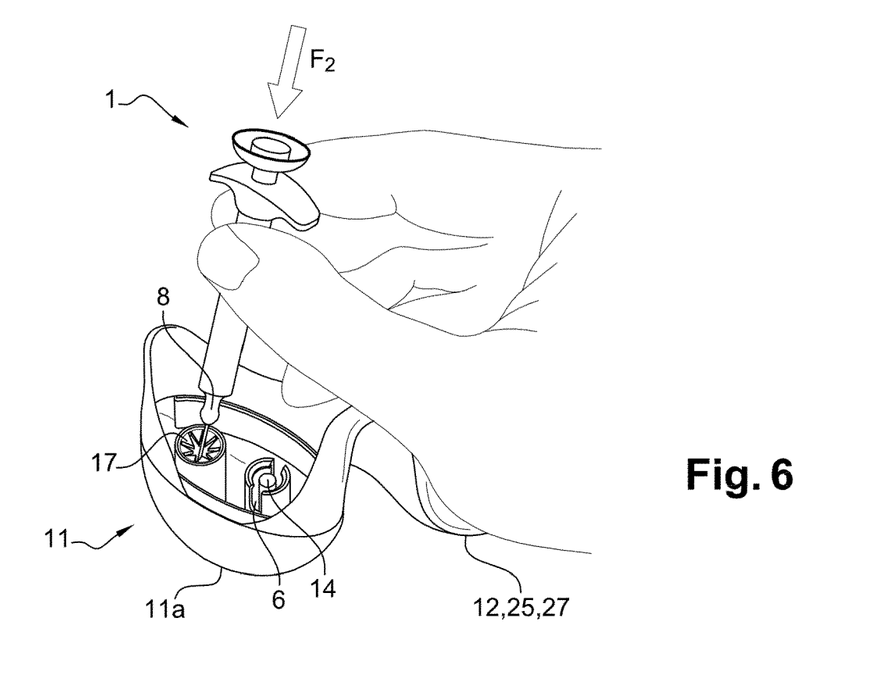
FIG. 6 is a perspective view of the step of repositioning the drug delivery device after use inside the packaging of FIG. 2.

Once the injection is completed, the user may approach the distal end of the used needle to the elongated lodging 17, and insert at least a distal part of the needle inside the second cavity 17a and the inner plug 19, so as to embed the distal part of the needle therein. The distal end of the needle is therefore protected and accidental needle stick injuries are avoided. Moreover, the drug delivery device 1 is maintained in a stable position.

The user may then close the packaging by covering the used drug delivery device 1 with the envelope 12 and may reseal the opening 13. The user may then transport the used drug delivery device 1 safely until he is able to throw the whole packaging away in a specific container.

Figure 7:
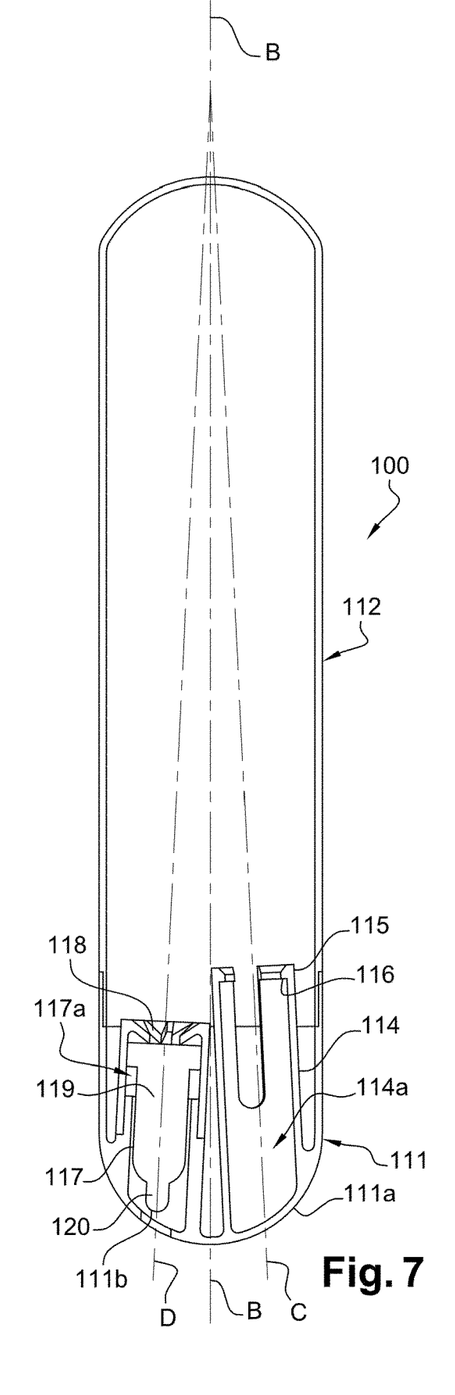
FIG. 7 is a cross section view of a second embodiment of a packaging of the invention.
Figure 8:
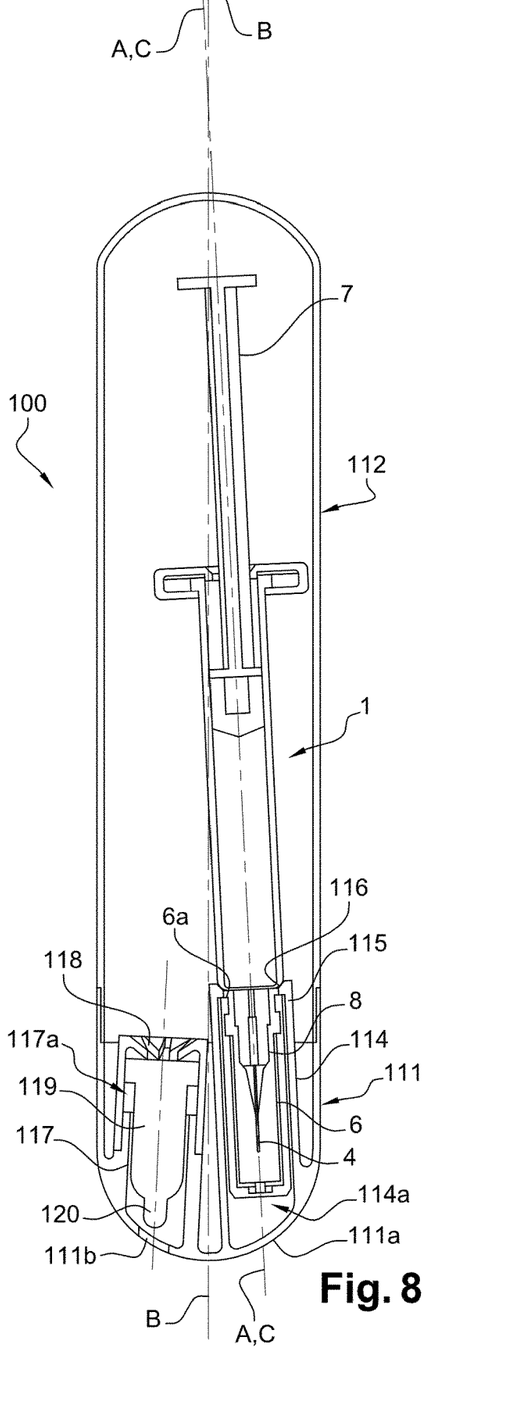
FIG. 8 is a cross section view of the packaging of FIG. 7 with the shield of a drug delivery device received in the first holding means or first holding element.
Figure 9:
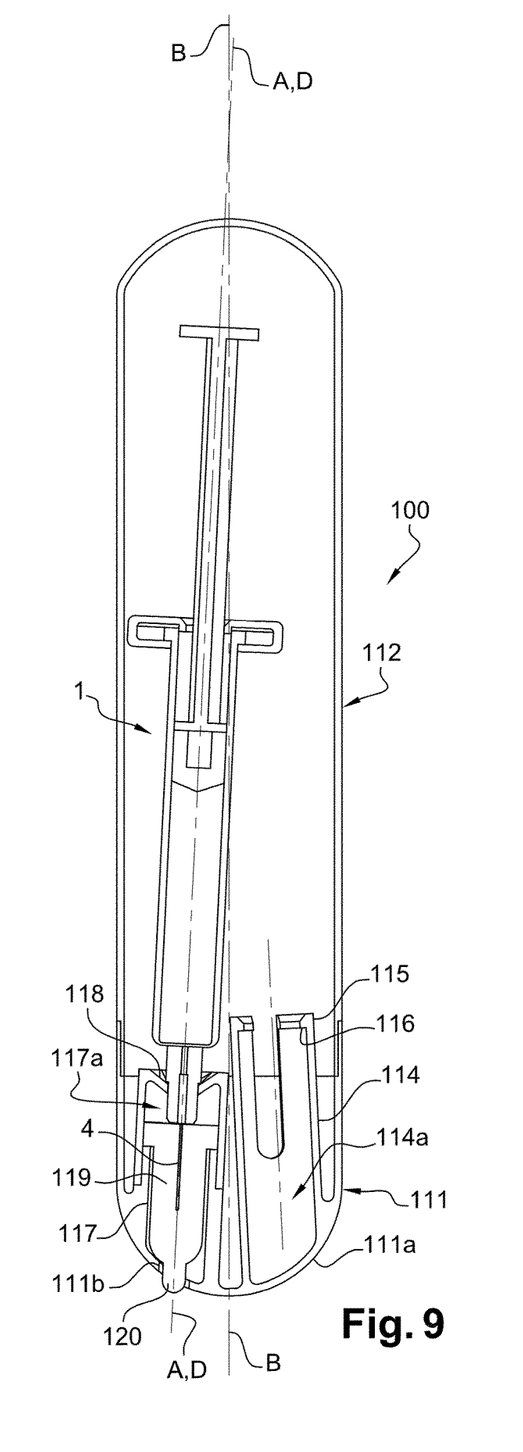
FIG. 9 is a cross section view of the packaging of FIG. 7 with the needle and a distal part of the distal tip received in the second holding means or second holding element.

With reference to FIGS. 7-9 is shown a second embodiment of the packaging of the invention, in which the first longitudinal axis C and the second longitudinal axis D are inclined towards the central longitudinal axis B of the envelope and in which the support and the envelope form altogether a rigid case. Suitable materials for forming the rigid case may be selected from polypropylene, polyoxymethylene, polycarbonate, acrylonitrile butadiene styrene and/or combinations thereof.

The packaging 100 of FIGS. 7-9 comprises a support 111 and an envelope 112, both made of a rigid material. The support 111 may be closed by the envelope 112 by friction fit engagement of the support 111 in the envelope 112. On FIGS. 7-9, the packaging 100 is shown in a closed configuration and therefore forms a rigid case capable of receiving a prefilled drug delivery device in a before-use storage configuration and/or in an after-use storage configuration.

With reference to FIGS. 7-9, the support 111 comprises a first cavity 114a defined by an elongate casing 114 extending proximally from the support 111 along a first longitudinal axis C. The first cavity 114a is configured to receive the shield 6 of the drug delivery device 1 in a before-use storage configuration of the drug delivery device 1, as shown in FIG. 8. The distal end of the elongate casing 114 is closed by a wall 111a of the support 111 and is therefore fixed to the support 111 in a permanent way. In the example shown, the elongate casing 114 has a cylindrical shape and is provided at its proximal end with flexible legs 115 provided with an inner rim 116. With reference to FIG. 8, the drug delivery device 1 is in its before-use storage configuration and is inserted in the support 111 via its shield 6 being retained within the first cavity 114a thanks to the flexible legs 115 being snap-fitted onto the proximal end 6a of the shield 6.

Still with reference to FIGS. 7-9, the support 111 comprises a second cavity 117a defined by an elongated lodging 117 extending proximally from the support 111 along a second longitudinal axis D. The second cavity 117a is shaped and dimensioned so as to be capable of receiving the used needle 4 and a distal part of the distal tip 8 of the drug delivery device 1 after use. On the example shown, the elongated lodging 117 has a cylindrical shape and extends from the wall 111a of the support 111. The elongated lodging 117 is provided at its proximal end with radial flexible tongs 118. At the distal end of the elongated lodging 117, the wall 111a of the support 111 is provided with an open channel 111b allowing the distal end of the second cavity 117a to communicate with the exterior of the packaging 100.

The second cavity 117a further includes an inner plug 119. The inner plug 119 is preferably made of a soft material such as rubber or an elastomeric polymer. In the example shown, the distal end of the inner plug 119 is provided with a protruding part, under the form of a peg 120. As will appear later in the description, the inner plug 119 is configured so as to be capable of sliding within the second cavity 117a along the second longitudinal axis D, and the peg 120 is shaped and dimensioned so as to be capable of circulating within the open channel 111b. In a before-use position of the packaging 100 or in the before-use storage configuration of the drug delivery device 1, the peg 120 is contained within the second cavity 117a and is neither visible nor feelable by a user.

With reference to FIG. 9, in the after-use storage configuration of the drug delivery device 1, the whole needle 4 and a distal part of the distal tip 8 of the drug delivery device 1 are received in the second cavity 117a. The distal part of the needle 4 is embedded in the inner plug 119. Moreover, the flexible tongs 118 retain the distal tip 8 inside the second cavity by 117a friction-fit engagement or retention teeth engagement.

In addition, the inner plug 119 has been pushed distally in the second cavity 117a, upon the pressure exerted by the distal tip 8 of the drug delivery device 1 coming in contact with a proximal end of the inner plug 119, thereby causing the peg 120 to move from a retracted position located within the second cavity 117a, as shown in FIG. 7 or 8, to an exposed position, at a distal end of the open channel 111b and close to the exterior of the packaging 100, where said peg 120 may be seen and/or felt by a user, as shown in FIG. 9.

As appears from FIGS. 7-9, the proximal end of the elongate casing 114 extends beyond the proximal end of the elongated lodging 117 in the proximal direction and further extends beyond the proximal end of the support 111 in the proximal direction.

As appears from FIG. 7, the envelope 112 extends proximally from the support 111 along a central longitudinal axis B. The first and second cavities (114a, 117a) are located on either side of a plane including the central longitudinal axis B. The first longitudinal axis C of the first cavity 114a and the second longitudinal axis D of the second cavity 117a are both inclined towards the central longitudinal axis B. As will appear from the description below, such an arrangement of the first and second cavities (114a, 117a) allow the drug delivery device 1 to be held sufficiently away from a wall of the envelope 112 when said drug delivery device 1 is stored within the packaging 100.

With reference to FIGS. 8-9, the use of the packaging 100 will now be described.

The packaging 100 is provided to a user in the before-use storage configuration of the drug delivery device 1, as shown in FIG. 8. The drug delivery device 1 is inserted in the support 111 via its shield 6 being retained within the first cavity 114a with the flexible legs 115 snap-fitted onto a proximal end 6a of the shield 6. In this configuration, the longitudinal axis A of the drug delivery device 1 and the first longitudinal axis C of the first cavity 114a are confounded. As a result, a proximal end of the container of the drug delivery device 1 is substantially located on the central longitudinal axis B of the envelope 112. As appears from FIG. 8, the drug delivery device 1 is as a consequence maintained at a certain distance away from the walls of the envelope 112. Moreover, the drug delivery device 1 is maintained in a stable position thanks to its shield 6 being safely secured within the first cavity 114a.

The user is therefore ensured that the drug delivery device 1 has not been in contact with the walls of the envelope 112 during the storage and that potential contamination of the drug delivery device has been avoided.

In this position also, the peg 120 is in a retracted position, within the second cavity 117a, where it is hidden from the view of the user.

When the user is ready to proceed to the injection, he may open the rigid case formed by the support 111 and the envelope 112 by removing the envelope 112 from the support 111. The user then removes the drug delivery device 1 from the first cavity 114a, while the shield 6 remains retained within said first cavity 114a thanks to the flexible legs 115 being snap-fitted onto the proximal end 6a of the shield 6. The user may pull on the drug delivery device 1 with one hand, while maintaining the support 111 with the other hand. The step of removing the shield 6 from the needle 4 is therefore facilitated for people suffering from arthritis for example. The needle 4 is therefore uncovered and the user may use the device in order to proceed to the injection. In addition, since the proximal end of the elongate casing 114 extends beyond the proximal ends of the elongated lodging 117 and of the support 111, the risk that the drug delivery device 1 touch the support 111 and/or the elongated lodging 117 when the drug delivery device 1 is removed from the elongate casing 114 is reduced. The risk that the drug delivery device 1 be contaminated before injection is therefore decreased.

Once the injection is completed, the user may approach the distal end of the used needle 4 towards the second cavity 117a. The user inserts the needle 4 inside the second cavity 117a and inside the inner plug 119 so as to embed the needle 4 therein. During this step, the distal end of the distal tip 8 comes in contact with the proximal end of the inner plug 119. While the user continues to push distally on the drug delivery device 1, the distal end of the distal tip 8 pushes the inner plug 119 which is caused to slide distally within the second cavity 117a. As a result, the peg 120 is caused to move distally and enters the open channel 111b of the wall 111a of the support 111.

As shown in FIG. 9, when the drug delivery device 1 is in its after-use storage configuration, the peg 120 protrudes outside the open channel 111b and becomes visible and feelable to the user. The peg 120 has therefore moved from its retracted position to its exposed position. In this configuration, the distal end of the needle 4 is protected and accidental needle stick injuries are avoided. Moreover, the drug delivery device 1 is maintained in a stable position thanks to the flexible tongs 118 retaining the distal part of the distal tip 8 within the second cavity 117a.

The user may then close the packaging 100 back by covering the used drug delivery device 1 with the envelope 112 and fit the envelope 112 on the support 111. In this configuration, as shown in FIG. 9, the longitudinal axis A of the drug delivery device 1 and the second longitudinal axis D of the second cavity 117a are confounded and a proximal end of the container of the drug delivery device 1 is substantially located on the central longitudinal axis B of the envelope 112, thereby allowing the used drug delivery device 1 to be maintained at a certain distance away from the walls of the envelope 112.

The arrangement of the first and second cavities (114a; 117a) in the support 111, with their respective longitudinal axes (C, D) inclined towards the central longitudinal axis B of the envelope 112 allows the drug delivery device 1 to be held sufficiently away from a wall of the envelope 112 when said drug delivery device 1 is stored within the packaging, while rendering the packaging 100 compact and easy to transport. In particular, the inclination of the elongate casing 114 and/or of the elongated lodging 117 allows obtaining a compact radial design for the packaging 100, even if the drug delivery device 1 stored therein comprises an extended flange.

The user may therefore transport the used drug delivery device 1 in the rigid case formed by the support 111 and envelope 112 safely until he is able to throw the whole packaging 100 away in an appropriate container.

The envelope of the packaging may further comprise information such as instructions for use.

Figures 13, 14:
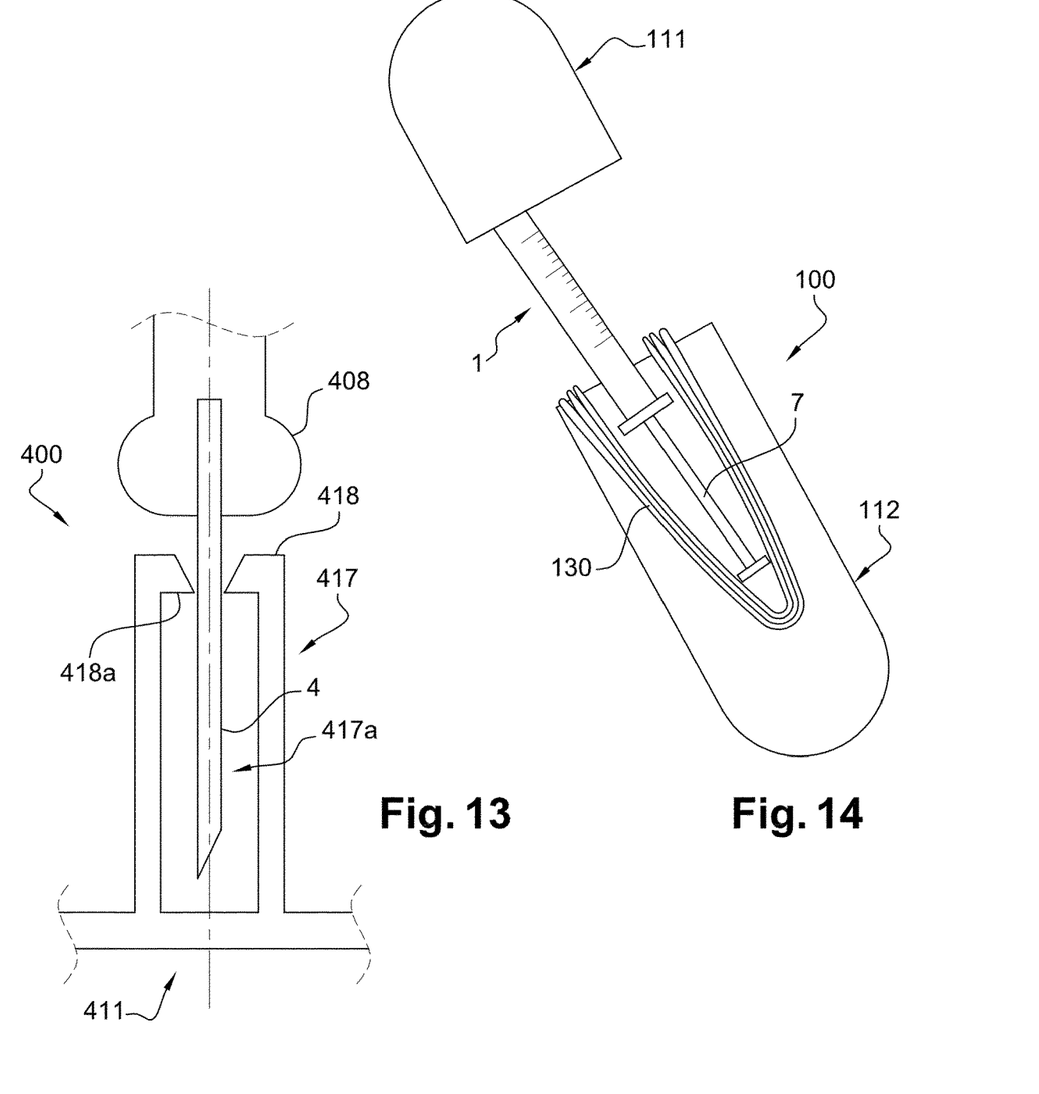
FIG. 13 is an alternative embodiment of a second cavity of the packaging of the invention.
FIG. 14 is a side view of the packaging of FIGS. 7-9 provided with a folded sheet bearing information such as instructions for use.

With reference to FIG. 14, is shown the packaging 100 of FIGS. 7-9, further comprising a sheet 130, for example made of paper. The sheet 130 may contain information such as instructions for use. In the before-use storage configuration of the drug delivery device 1, the sheet 130 is folded on itself and over the piston rod 7 of the drug delivery device 1, so that it is made directly available to the user when the user proceeds to the opening of the packaging 100 as shown on FIG. 14. For example, the sheet 130 may be folded in a way so that said sheet 130 pops up from the packaging 100 when the user removes the envelope 112 from the support 111. The use of the packaging is therefore facilitated for the user, who will not waste time searching for the instructions for use.

Figure 15:
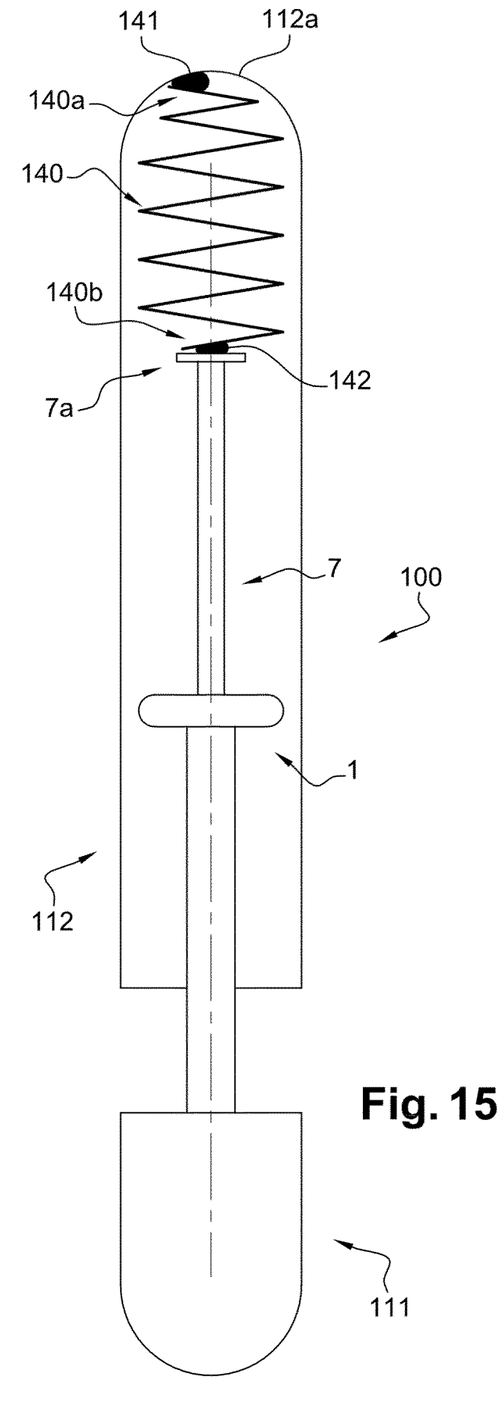
FIG. 15 is a schematic side view of another embodiment of the packaging of FIGS. 7-9 provided with a folded sheet bearing information such as instructions for use, at the time the user begins to open the packaging.
Figure 16:
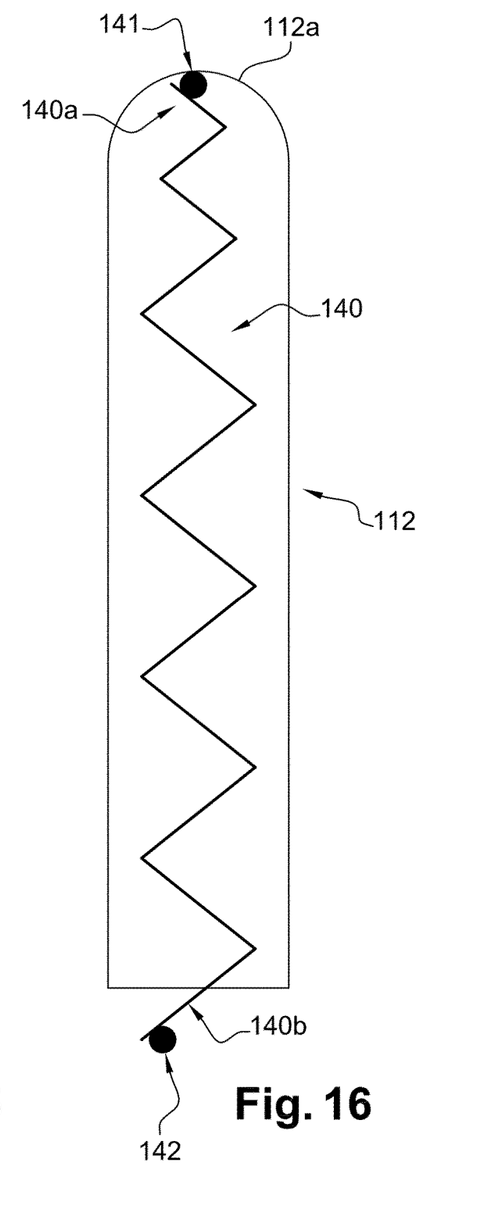
FIG. 16 is a schematic side view of the packaging of FIG. 15 once the packaging is completely open.

With reference to FIGS. 15 and 16, is shown the packaging of FIGS. 7-9, further comprising a sheet 140, for example made of paper. The sheet 140 may contain information such as instructions for use. In the before-use storage configuration of the drug delivery device 1, the sheet 140 is folded on itself in a concertinaed way and sandwiched between a proximal end 7a of the plunger rod 7 and an inner surface of a proximal wall 112a of the envelope 112. A first glue dot 141 links a proximal end 140a of the folded sheet 140 to the inner surface of the proximal wall 112a. A second glue dot 142 links a distal end 140b of the folded sheet 140 to the proximal end 7a of the piston rod 7. The first glue dot 141 shows an attachment force greater than that of the second glue dot 142. As a result, when the user pulls on the envelope 112 in a view of opening the packaging 100, the sheet 140 slowly unfolds as its proximal end 140a remains attached to the inner surface of the proximal wall 112a of the envelope 112 and its distal end 140b is drawn in the distal direction together with the piston rod 7, as shown on FIG. 15. When the sheet 140 is completely unfolded, the user releases the second glue dot 142 from the plunger rod, as shown in FIG. 16. The user may then remove completely the sheet 140 from the envelope 112 by keeping on pulling on the distal end 140b of the sheet 140, until the first glue dot 141 comes off and separates from the inner surface of the proximal wall 112a of the envelope 112. The use of the packaging is therefore facilitated for the user, who will not waste time searching for the instructions for use.

Figure 10:
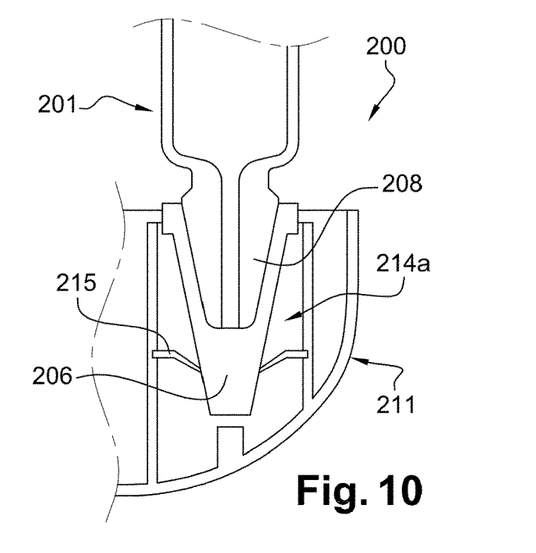
FIG. 10 is a partial cross section view of a shield of a drug delivery device received in the first holding means or first holding element in the case where the distal tip of the drug delivery device is free of any needle in the before-use storage configuration of said drug delivery device.
Figure 11:
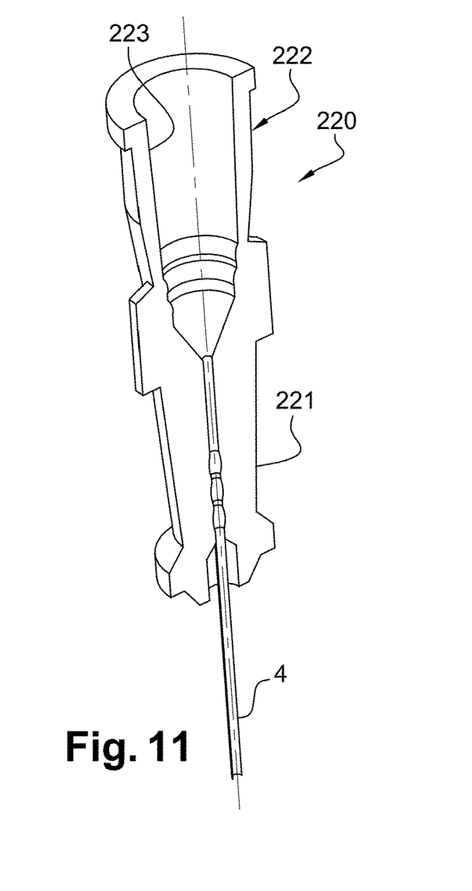
FIG. 11 is a perspective cross section view of a needle hub that may be mounted on the distal tip of the drug delivery device of FIG. 10.

With reference to FIGS. 10 and 11, are shown partial views of an alternative embodiment of a packaging 200 of the invention, when the distal tip 208 of the drug delivery device 201 is free of any needle in the before-use storage configuration of the drug delivery device 201. In such embodiments, the shield 206 of the drug delivery device 201 may be formed from a soft material, such as a rubber or an elastomeric polymer.

As shown in FIG. 10, the shield 206 covers the distal tip 208 of the drug delivery device 201 and is received within the first cavity 214a of the support 211 of the packaging 200 when the drug delivery device 201 is in its before-use storage configuration. The shield 206 may be retained within the first cavity 214a by means of flexible legs 215 forming first gripping means or first gripping element.

In such embodiments, the packaging 200 may therefore further comprise a needle hub 220, as shown in FIG. 11. The needle hub 220 comprises a hub 221 bearing a needle 4 and a proximal sleeve 222 defining a conical recess 223 configured to be fitted onto the distal tip 208.

In such embodiments, when the user is ready to proceed to the injection, he may remove the drug delivery device 201 from the first cavity 214a while the shield 206 remains retained within said first cavity 214a thanks to the flexible legs 215 being snap-fitted onto the shield 206. The user has therefore in hands a drug delivery device 201 provided with a distal tip 208 free of any needle. The user may then grasp the needle hub 220 provided in the packaging 200 and mount said needle hub 220 onto the distal tip 208 by fitting the conical recess 223 onto said distal tip 208. The user is thereby provided with a drug delivery device 201 provided with a needle 4 and he may proceed to the injection.

Once the injection is completed, the user may simply insert the used needle into the second cavity (not shown) in the same manner as described in the above description for embodiments of FIGS. 2-9, without having to remove the needle hub 220 from the distal tip 208.

Figure 12:
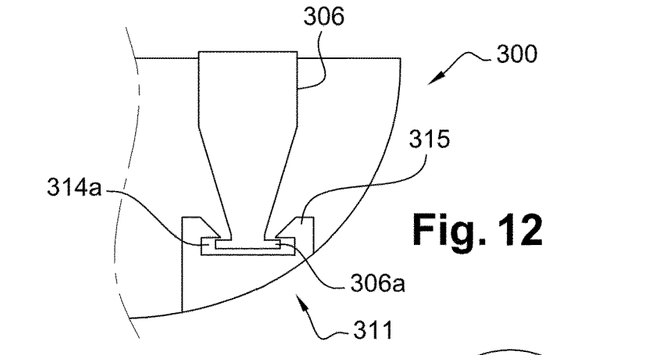
FIG. 12 is a cross section view of an alternative embodiment of the first cavity of the packaging of the invention.

With reference to FIG. 12 is shown an alternative embodiment of a first cavity 314a of a support 311 of a packaging 300 of the invention in which the first gripping means or first gripping element retain the shield 306 of the drug delivery device (not shown) fixed to said first cavity 314a thanks to a cooperation with a distal end of said shield 306.

With reference to this Figure, the first cavity 314a is defined by a port 314 comprising flexible legs 315. The shield 306 is provided with a distal outer rim 306a. As shown in this Figure, in the before-use storage configuration of the drug delivery device, the flexible legs 315 are snap-fitted onto the distal outer rim 306a of the shield 306, thereby forming first gripping means or first gripping element retaining the shield 306 fixed to the cavity 314a.

With reference to FIG. 13, is shown an alternative embodiment of a second cavity 417a of a support 411 of a packaging 400 of the invention in which the second gripping means or second gripping element are configured for being snap-fitted onto the needle 4. With reference to this Figure, the second cavity 417a is defined by an elongated lodging 417 configured for receiving at least a distal part of the needle 4. The elongated lodging 417 is provided at its proximal end with flexible legs 418 provided with inner rims 418a. The flexible legs 418 and their inner rims 418a are made of a flexible metal allowing and are capable of being snap-fitted to the needle 4 so as to retain said needle 4 within the second cavity 417.

The packaging of the invention allows safely storing and transporting a prefilled drug delivery device, before and after use.

The invention claimed is:

1. Packaging for storing at least one drug delivery device comprising a container provided at its distal end with a distal tip covered by a shield in a before-use storage configuration of the drug delivery device, said shield configured to be removed from said distal tip at time of use and a distal end of said distal tip configured to bear a needle during use of the drug delivery device, the packaging comprising:
   a support comprising at least:
      one first holding element configured for receiving at least part of said shield in the before-use storage configuration of said drug delivery device;
      one second holding element configured for receiving at least a distal part of said needle when said needle is borne by said distal tip in an after-use storage configuration of said drug delivery device; and
      an envelope configured to enclose said drug delivery device, when said shield is received in said first holding element in the before-use storage configuration of the drug delivery device and when said distal part of said needle is received in said second holding element in the after-use storage configuration of said drug delivery device, said envelope configured to be closed by said support.

2. The packaging according to claim 1, wherein said second holding element is configured for further receiving at least a distal part of said distal tip.

3. The packaging according to claim 1, wherein said distal tip is free of any needle in the before-use storage configuration of said drug delivery device, said packaging further comprising a needle hub bearing a needle, said needle hub configured for mounting onto a distal end of said distal tip once the shield has been removed from said distal tip.

4. The packaging according to claim 1, wherein said first holding element comprises:
a first cavity configured to receive at least part of said shield; and
a first gripping element configured to retain said shield fixed to said cavity.

5. The packaging according to claim 4, wherein a proximal end of said shield is attached onto said distal tip, and
wherein said first gripping element comprises flexible legs configured to be snap-fitted onto said proximal end of said shield.

6. The packaging according to claim 4, wherein said second holding element comprises:
a second cavity configured to receive said needle and at least a distal part of said distal tip; and
a second gripping element configured to retain said needle and said distal part of said distal tip within said second cavity.

7. The packaging according to claim 6, wherein said second gripping element comprises flexible tongs retaining said distal tip by friction-fit engagement.

8. The packaging according to claim 6, wherein said second cavity further comprises an inner plug configured for embedding a distal part of the needle.

9. The packaging according to claim 1, wherein said support and said envelope form a rigid case.

10. The packaging according to claim 6, wherein said first cavity has an elongated shape extending proximally from the support along a first longitudinal axis and said second cavity has an elongated shape extending proximally from the support along a second longitudinal axis.

11. The packaging according to claim 10, wherein said first longitudinal axis and said second longitudinal axis are parallel to each other.

12. The packaging according to claim 10, wherein said envelope extends proximally from said support along a central longitudinal axis,
wherein said first and second cavities are located on either side of a plane including said central longitudinal axis, and
wherein said first and second longitudinal axes are inclined toward said central longitudinal axis, so that a proximal end of the container of said drug delivery device is substantially located on the central longitudinal axis when said shield is received in said first holding element in the before-use storage configuration of the drug delivery device or when said distal part of said needle is received in said second holding element in the after-use storage configuration of said drug delivery device.

13. The packaging according to claim 1, further comprising a tactile or visual indicator configured to inform a user that the distal part of said needle is received in said second holding element in the after-use storage configuration of said drug delivery device.

14. The packaging according to claim 13, wherein said indicator comprises a peg configured to circulate in an open channel provided in a wall of the support and communicating with said second holding element, said peg configured to move from a retracted position, in which said peg is neither visible nor feelable by a user, to an exposed position, in which said peg may be seen or felt by the user, said peg configured to move from said retracted position to said exposed position upon insertion of the distal part of said needle into said second cavity.

15. The packaging according to claim 1, wherein said envelope comprises a film having a resealable opening.

16. The packaging according to claim 1, further comprising medical items selected from anesthetic pads, alcohol swabs, sticky plasters and combinations thereof located within the envelope.

17. The packaging according to claim 1, further comprising a sheet bearing instructions for use, said sheet being folded on itself and positioned between the drug delivery device stored in said packaging in its before-use storage configuration and an inner wall of the envelope, so that said sheet pops up from the packaging when a user removes the envelope from the support.

* * * * *